United States Patent [19]

Giolito

[11] Patent Number: 4,492,660

[45] Date of Patent: Jan. 8, 1985

[54] LOW TEMPERATURE STABLE TERT-BUTYLPHENYL DIPHENYL PHOSPHATE

[75] Inventor: Silvio L. Giolito, Whitestone, N.Y.

[73] Assignee: Stauffer Chemical Company, Westport, Conn.

[21] Appl. No.: 529,466

[22] Filed: Sep. 6, 1983

Related U.S. Application Data

[62] Division of Ser. No. 279,389, Jul. 1, 1981, Pat. No. 4,414,161.

[51] Int. Cl.³ .............................................. C07F 9/09
[52] U.S. Cl. ................................................... 260/966
[58] Field of Search .......................................... 260/966

[56] References Cited

FOREIGN PATENT DOCUMENTS 2833342 2/1980 Fed. Rep. of Germany ...... 260/966

Primary Examiner—Anton H. Sutto
Attorney, Agent, or Firm—Vivienne T. White

[57] ABSTRACT

A process for producing tert-butylphenyl diphenyl phosphate which is stable at low temperature by a process wherein phenol is butylated to produce tert-butylphenol which is isomerized to produce mixed meta and para isomers thereof, and which thereafter is alkylated with isobutylene to produce tert-butylphenol having a $C_4/\phi$ ratio of about 0.62. The tert-butylphenol is then phosphorylated to the tert-butylphenyl diphenyl phosphate meta/para mixture with phosphorus oxychloride. The disclosed process provides a tert-butylphenyl diphenyl phosphate which will not freeze or gel at low temperatures.

4 Claims, No Drawings

LOW TEMPERATURE STABLE TERT-BUTYLPHENYL DIPHENYL PHOSPHATE

This is a division of application Ser. No. 279,389 filed July 1, 1981 now U.S. Pat. No. 4,414,161.

BACKGROUND OF THE INVENTION

1. Field of the Invention

The present invention relates to the preparation of tert-butylphenyl diphenyl phosphate. More particularly, the present invention relates to the preparation of a meta/para isomer mixed tert-butylphenyl diphenyl composition having low temperature stability.

2. Related Art

It is known to produce tert-butylphenyl diphenyl phosphate by the process of alkylating a phenol with isobutylene and thereafter phosphorylating the tert-butylphenol product to the tert-butylphenyl diphenyl phosphate product with phosphorus oxychloride.

As manufactured by the above process, the phosphate ester which is primarily composed of the para-isomer has a tendency to crystallize upon low temperature storage when produced from a tert-butylphenol composition containing a high concentration of para-tert-butylphenol (a/k/a p-tert-butylphenol).

Meta tert-alkylphenols have been prepared by the isomerization of tert-alkylphenols in the presence of trifluoromethane sulfonic acid, see U.S. Pat. No. 4,103,096 incorporated herein by reference.

SUMMARY OF THE INVENTION

In accordance with this invention there is provided a method of preparing tert-butylphenyl diphenyl phosphate which will not crystallize upon low temperature storage. It has been discovered that stable low temperature tert-butylphenyl diphenyl phosphate can be produced utilizing the process of this invention.

The process of the invention comprises catalytically alkylating a phenol with isobutylene to produce tert-butylphenol and thereafter catalytically isomerizing the tert-butylphenol to produce a meta/para isomer mixture which is realkylated to achieve the desired $C_4/\phi$ ($\phi$=phenyl) mole ratio and hence a desired phosphate ester viscosity; and then phosphorylated with phosphorous oxychloride to form the tert-butylphenyl diphenyl phosphate product having stable low temperature properties.

DETAILED DESCRIPTION OF THE INVENTION

The alkylphenols may be prepared by any of a number of methods known in the art. In perhaps the best known method, an alkylphenol is prepared by alkylating phenol with an olefin in the presence of an appropriate catalyst at a temperature ranging from about 100° to about 250° C. and preferably from 120°-190° C. The olefin/phenol molar ratio should range from about 0.2/1 to about 2/1. Appropriate catalysts for this purpose include Friedel-Crafts catalysts such as aluminum chloride, boron trifluoride, and the like; acid catalysts such as sulfonic acid, para-toluene sulfonic acid, and the like; and acidic clays such as montmorillonite clay, and the like.

The product of the alkylation reaction will, in most cases, consist of a mixture of several alkylphenol isomers. For example, when phenol is alkylated with isobutylene, the product can include ortho-tertiary-butylphenol, para-tertiary-butylphenol, meta-tertiary-butylphenol, 2,4-ditertiary-butylphenol, 2,4,6-tri-tertiary-butylphenol, and the like. The amount of the meta isomers present in these mixtures, however, is often so low as to be non-detectable by the usual chromatographic analysis techniques.

The invention is particularly directed to a method of stabilizing the low temperature properties of tert-butylphenyl diphenyl phosphate having a SUS (Saybolt Universal Seconds) viscosity of 550 also known by the tradename FYRQUEL ®-550. The process is also applicable to producing low temperature stable high viscosity fluid comprising tert-butylphenyl diphenyl phosphate in general. The term "low temperature stability" is used herein to mean a tert-butylphenyl diphenyl phosphate product which will not crystallize at temperatures of about 0° C.

In the process of the invention, a phenol is butylated to produce p-tert-butylphenol with isobutylene. The p-tert butylphenol is then catalytically isomerized to produce a mixture of para and meta tert-butylphenols. Isomerization of the tert-butylphenol mixture with the catalyst leads to a partial dealkylization of the tert-butylphenol. The partially dealkylated mixture if thereafter phosphorylated would not produce a meta/para-tert-butylphenyl diphenyl phosphate product of the required SUS viscosity level It is therefore necessary to readjust the $C_4/\phi$ ratio of the mixture to an acceptable molar ratio by realkylation with isobutylene so as to provide a final product having the requisite viscosity (measured as SUS). The viscosity (in SUS units) relates directly to the $C_4/\phi$ mole ratio of the phosphate ester product.

The reaction by which the non-meta-alkylphenols are isomerized to a meta/para-alkylphenol may be conducted under vacuum, atmospheric or at elevated pressures. The temperature at which the reaction is conducted varies from about 120° C. to about the reflux temperature of the reaction mixture (about 190° C.). The reflux temperature will, of course, vary in accordance with the pressure at which the reaction is being conducted.

In accordance with this invention, the para tert-butylphenol which is to be isomerized is brought into contact with a trifluoromethane sulfonic acid catalyst at an elevated temperature and for a period of time sufficient to promote some isomerization of the p-tert-butylphenol isomer to a meta/para tert-butylphenol isomer mixture.

Contact of the tert-butylphenol with the trifluoromethane sulfonic acid catalyst may be accomplished by any of those techniques known in the art for contacting chemical reactants with catalysts. Since trifluoromethane sulfonic acid is readily soluble in phenol and many alkylphenols, a preferred technique is to add the trifluoromethane sulfonic acid directly to the reaction mixture in liquid form. The trifluoromethane sulfonic acid may be added neat or as a solution in phenol, or in other appropriate solvents. Since the total amount of trifluoromethane sulfonic acid required is generally quite small, it is most convenient to add the catalyst to the reaction mixture as a dilute solution.

When used in the form of a liquid which is miscible with the other components of the reaction mixture, the trifluoromethane sulfonic acid may be easily added or continuously metered to the reaction mixture. When used in this form, the trifluoromethane sulfonic acid may also be readily removed from the product upon completion of the reaction. Thus, for example, upon completion of the reaction, the trifluoromethane sulfonic acid may be left un-neutralized or neutralized with any convenient base. Then, when the reaction mass is subsequently purified by distillation, the neutralized or un-neutralized trifluoromethane sulfonic acid remains in the distillation bottoms, which may then be discarded. When left in the final product, it does not interfere with the phosphorylation reaction with phosphorous oxychloride.

The trifluoromethane sulfonic acid may also be added to the reaction mixture in the form of a heterogenous catalyst such as that formed by impregnating a clay or other particulate substrate with the trifluoromethane sulfonic acid or by absorbing the trifluoromethane sulfonic acid into a clay or other particulate substrate. The advantages offered by this type of catalyst such as, for example, the ability to recover and recycle the catalyst, often outweigh the inconvenience associated with the use of hetergeneous catalysts.

The concentration of trifluoromethane sulfonic acid usually will vary in accordance with many factors such as the design of the reactor being used, the temperature and pressure at which the reaction is being conducted, the mode of the reaction (batch or continuous), the reaction rate desired, the presence of solvent, and other factors, all of which are easily determined by one skilled in the art. It has been found that trifluoromethane sulfonic acid concentration ranging from about 0.025% to about 0.50% by weight of alkylphenol are effective under most circumstances although concentrations ranging from about 0.05% to 0.20% are preferred.

The time period required to effect isomerization of the p-tert-butylphenol isomer to a meta/para tert-butylphenol isomer mixture will vary in accordance with a number of factors such as, for example, the degree of isomerization desired. Additional factors, which also effect the time required are the concentration of trifluoromethane sulfonic acid in the reaction mixture and the temperature at which the reaction is being conducted. Satisfactory results may generally be achieved in time periods ranging from about 1 to about 3 hours. Where it is desired to approach equilibrium conditions, time periods of up to 10 hours or more may be required.

Although the reaction may be conducted over a relatively wide temperature range such as from about 120° C. to the reflux temperature of the reaction mixture (about 185°–190° C. at atmospheric pressure), it is preferred to conduct the isomerization reaction at reflux temperature. The reflux temperature does, of course, vary in accordance with the pressure at which the reaction is being conducted. The pressure, in turn, may vary from vacuum to several atmospheres depending on the need of the individual practitioner.

A more economical method of conducting the isomerization of the tert-butylphenol para-isomer is to initially conduct the alkylation of the phenol with a TSA catalyst (toluene sulfonic acid) and to utilize the trifluoromethane sulfonic acid catalyst for the isomerization and subsequent realkylation process.

As indicated previously, the isomerization of the tert-butylphenol para-isomer with the trifluoromethane sulfonic acid catalyst leads to the partial dealkylization of the tert-butylphenol mixture. Therefore, depending on the specific viscosity of the phosphate ester product desired, it may be necessary to adjust the $C_4/\phi$ ratio of the isomerized tert-butylphenol meta para-isomer mixture with isobutylene.

In a method of producing the mixed para/meta tert-butylphenyl diphenyl phosphate having a SUS viscosity of 550, in accordance with the invention, phenol is alkylated in the presence of a catalyst such as toluene sulfonic acid or trifluoromethane sulfonic acid to a $C_4/\phi$ ratio of from 0.70 to 0.90 and preferably from 0.75 to 0.85 to produce a predominantly p-isomer tert-butylphenol with essentially no meta isomer. Thereafter the p-tert-butylphenol is catalytically isomerized utilizing the trifluoromethane sulfonic acid catalyst to obtain a meta/para-isomer mixture having a meta/para ratio of from 0.50 to 0.70 and preferably from 0.55 to 0.65. When the $C_4/\phi$ ratio has dropped to a value within the range of from about 0.4–0.5, the para/meta mixture is then realkylated with isobutylene at a temperature of about 120° to about 190° C. to give a $C_4/\phi$ of from 0.55 to 0.85 and preferably from 0.60 to 0.65 and a meta/para ratio of from about 0.25 to about 0.50.

After realkylating with isobutylene to the desired $C_4/\phi$ ratio, the isomer mixture is phosphorylated with phosphorus oxychloride to produce a low temperature, stable tert-butylphenyl diphenyl phosphate product having the desired SUS viscosity.

With strict monitoring (process control) of the $C_4/\phi$ ratio of the realkylated tert-butylphenol mixture, the product having the desired SUS viscosity can be directly prepared. It is also possible, however, to produce a product of higher viscosity by the disclosed method and dilute it with a product of lower viscosity to produce the desired viscosity.

The phosphorylation of the alkylated phenol product, produced by the reaction of the phenol with the alkylating agent, may be carried out under a wide range of conventional phosphorylation reaction conditions. If the reaction is effected in the presence of a Lewis acid catalyst, this catalyst may be different from, but is preferably the same as, the catalyst used in the alkylation stage. The preferred phosphorylation catalyst is, however, anhydrous magnesium chloride. The proportion of catalyst present is preferably in the range of from 0.001% to 5% by weight, and especially from 0.05% to 1% by weight based on the weight of the phenol present in the alkylated phenol product reacted with the phosphorylating agent. The preferred phosphorylating agent is phosphorus oxychloride, but other phosphorylating agents such as phosphorus oxybromide or phosphoric acid may also be employed.

The phosphorylation is preferably carried out at a temperature in the range of from 100° to 190° C. A reaction temperature in the range of from 150° to 180° C. is particularly preferred in order to obviate the use of larger proportions of phosphorylating agent with respect to the alkylated phenol which may be necessary to secure good yields of the desired phosphate ester when operating the reaction at lower temperatures.

The proportion of the phosphorylating agent to that of the alkylated phenol may be varied within a wide range, depending on the nature of the reactants and the reaction conditions, but is preferably within the range of from 1 to 5 moles, and particularly within the range of from 3.0 to 3.5 moles, of alkylated phenol per mole of phosphorylating agent.

It would be obvious to one having skill in the art that low temperature stable tert-butylphenyl diphenyl phosphate products of varying viscosity can be produced utilizing the novel process of this invention.

The invention will be further illustrated in the following non-limiting example.

EXAMPLE

Low temperature stable tert-butylphenyl diphenyl phosphate comprising a meta/para isomer mixture was produced stepwise as follows:

Step I. A 282 grams (3.0 mole) amount of phenol was charged to a 1 liter 3 neck flask to which was added 0.28 grams (0.1%) of trifluoromethane sulfonic acid catalyst. The charge was stirred and heated to 150° C. A 139 grams (2.92 mole) amount of isobutylene gas was added as rapidly as it was absorbed. Analysis of the t-butylphenol mixture via Gas Chromotography showed the material to contain 71% a/k/a p-tert-butylphenol with a $C_4/\phi$ mole ratio of 0.81.

Step II. Thereafter 0.28 grams of the catalyst was added to the charge and the mixture was isomerized for two hours at reflux temperatures (190° C.). Analysis of the composition showed it to have a $C_4/\phi$ mole ratio of 0.47 with a meta tert-butylphenol content of 38.5%.

Step III. Then 26 grams (0.46 mole) of isobutylene gas was added to the charge and heated to a temperature of 150° C. in order to adjust the $C_4/\phi$ mole ratio to about 0.62 required for the high viscosity. The following Table provides an analysis of the products obtained in the above steps expressed where applicable in weight percent based on the total weight of the mixture.

TABLE 1

| Composition | Step 1 | Step 2 | Step 3 |
|---|---|---|---|
| phenol | 16.86 | 43.32 | 30.34 |
| ortho isomer | 3.16 | 1.68 | 1.92 |
| meta isomer | 0 | 19.11 | 16.18 |
| para isomer | 71.12 | 30.52 | 45.24 |
| 2,6 di* | 8.85 | 0.81 | 1.76 |
| 2,4 di* | — | 3.36 | 3.34 |
| 2,5 – 3,5 di* | — | 0.58 | 0.84 |
| tri* | — | 0.33 | 0.34 |
| $C_4/\phi$ ratio | 0.810 | 0.474 | 0.625 |
| meta/para ratio | 0 | 38.5/61.5 | 26.34/73.66 |

*tert butylphenol

Then 153.4 grams (1.0 mole) of $POCl_3$, and 0.5 grams of anhydrous magnesium chloride catalyst was added to the t-butylphenol mixture from Step III. The charge was heated gradually to 160° C. during which HCl gas was evolved. After 3¾ hours, an additional 3 ml. of $POCl_3$ was added and the charge was heated an additional hour at 160° C.

The tert-butylphenyl diphenyl phosphate mixture above was vacuum distilled and the distillate was washed twice with a 1% caustic solution for one hour at 65° C. and with water until neutral. The ester was distilled at 100° C./10 mm Hg. The finished ester had a SUS viscosity of 616 at about 38° C. and an acid number of 0.28. The ester was then diluted with a 150 SUS ester to a desired 550 SUS viscosity.

What is claimed is:

1. A low temperature, stable tert-butylphenyl diphenyl phosphate product which will not crystallize at temperatures of about 0° C., comprised of mixed meta/para isomers produced by (a) alkylating a phenol with isobutylene to produce a predominantly para-tert-butylphenol and (b) catalytically isomerizing the para-tert-butylphenol to produce a meta/para isomerized tert-butylphenol mixture; then (c) realkylating the isomerized tert-butylphenol mixture to obtain a desired $C_4/\phi$ ratio; and (d) phosphorylating the realkylated tert-butylphenol with a phosphorylating agent to produce a tert-butylphenyl diphenyl product characterized by low temperature stability.

2. The product of claim 1 further comprising a $C_4/\phi$ ratio of from about 0.55 to about 0.85.

3. The product of claim 1 wherein the meta/para ratio is from about 0.25 to about 0.50.

4. The product of claim 1 wherein the meta/para ratio is from about 0.25 to about 0.50.

* * * * *